(12) United States Patent
Beckman

(10) Patent No.: US 9,259,347 B2
(45) Date of Patent: Feb. 16, 2016

(54) BODILY COOLING FLUID TECHNIQUES

(71) Applicant: Christopher V. Beckman, San Diego, CA (US)

(72) Inventor: Christopher V. Beckman, San Diego, CA (US)

( * ) Notice: Subject to any disclaimer, the term of this patent is extended or adjusted under 35 U.S.C. 154(b) by 147 days.

(21) Appl. No.: 13/745,833

(22) Filed: Jan. 20, 2013

(65) Prior Publication Data
US 2014/0205554 A1    Jul. 24, 2014

(51) Int. Cl.
*A61F 7/00* (2006.01)
*A61F 7/02* (2006.01)

(52) U.S. Cl.
CPC ........... *A61F 7/00* (2013.01); *A61F 2007/0065* (2013.01); *A61F 2007/0068* (2013.01); *A61F 2007/0219* (2013.01); *A61F 2007/0234* (2013.01)

(58) Field of Classification Search
CPC ................ A61F 2007/0065; A61F 2007/0068; A61F 2007/0219; A61F 2007/0234; A61F 7/00
See application file for complete search history.

(56) References Cited

U.S. PATENT DOCUMENTS

| | | | | |
|---|---|---|---|---|
| 5,421,326 | A * | 6/1995 | Rankin | A62B 17/00 128/201.11 |
| 5,620,140 | A * | 4/1997 | Utter | B05B 9/0816 239/153 |
| 6,109,338 | A * | 8/2000 | Butzer | 165/46 |
| 7,089,995 | B2 * | 8/2006 | Koscheyev et al. | 165/46 |
| 2009/0133853 | A1 * | 5/2009 | Gammons | 165/104.11 |

OTHER PUBLICATIONS

Torii et al., (Br J sp Med 1992; 26(1):29-32).*
Serway. R. A., "Essentials of College Physics," 2007, Belmont, CA, Thomson Higher Education, pp. 252-254.
ASM International, Thermal Expansion, at Chapter 2; 9 pages.
Engineer's Handbook, Plastic Thermal Coefficients, retrieved from the internet at http://www.engineershandbook.com/Tableslplasticthermalexp.htm, retrieved on Mar. 18, 2015; 2 pages.
Bal Seal Engineering Inc., Coefficient of Thermal Expansion for Various Materials at Different Temperatures, retrieved from the internet at http://www.balseal.com/sites/default/files/tr18_020707131421.pdf, retrieved on Mar. 18, 2015, (2004); 6 pages.
Duffy, B.U. Physics (1999), Temperature and Thermal Expansion, retrieved from the internet at physics.bu.edu/~duffy/py105/Temperature.html, retrieved on Mar. 18, 2015; 3 pages.
Kenyon College, Department of Physics, 'sGravesande's Apparatus, retrieved from the internet at http://physics.kenyon.edu/EarlyApparatus/Thermodynamics/sGravesandes_Apparatus/sGravesandes_Apparatus.html, retrieved on Mar. 18, 2015; 3 pages.
Osha, Heat Stress Guide, retrieved from the internet at https://www.osha.gov/SLTC/emergencypreparedness/guides/heat.html, retrieved on Mar. 18, 2015; 3 pages.
Princeton University, Heat Stress Fact Sheet, retrieved from the internet at http://web.princeton.edu/sites/ehs/heatstress/heatstress.htm, retrieved on Mar. 18, 2015; 7 pages.
Weinmann, M., Hot on the inside, Emerg. Med. Serv. 32(7):34 (2003); 2 pages.
Lior Yankelson, MD, et al., Life-Threatening Events During Endurance Sports, Journal of the American College of Cardiology, vol. 64, Issue 5 (2014); 3 pages.

* cited by examiner

*Primary Examiner* — Brian-Yong Kwon
*Assistant Examiner* — Mark V Stevens

(57) ABSTRACT

New bodily cooling techniques are provided. In some aspects of the present invention, a new rapidly-evaporating cooling gel or fluid is sprayed or doused over or about an athlete's body and/or worn garments in thermal-reduction-optimized gravitational, diffusion and movement-induced patterns, to maximize cooling during exercise. In some aspects, a worn garment may serve as the matrix or platform for this distribution of the fluid. In other aspects, tuned, heat-absorbing port-controlling devices cause the release of the cooling gel or fluid from distribution tubes or other channels (e.g., integral to the flexible fabric itself) upon local underlying body heat exceeding a threshold, and resealing (halting release) upon body or regional heat dropping below a threshold. In still other aspects, heat-expanding sub-elements rise away from a body heat source toward a wider region for heat release, while other cooled sub-elements descend and exchange places with them, to absorb more body heat.

21 Claims, 13 Drawing Sheets

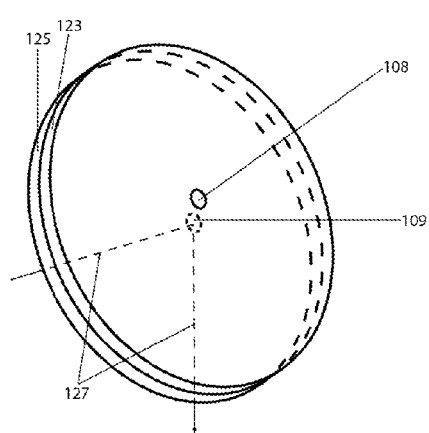
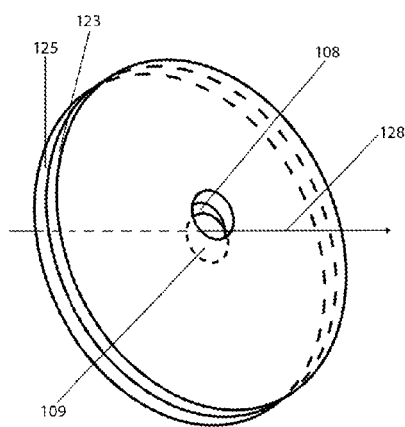
Fig. 1c
Fig. 1d
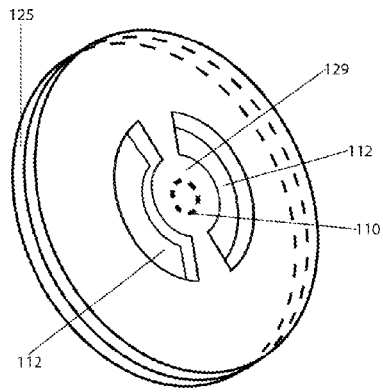
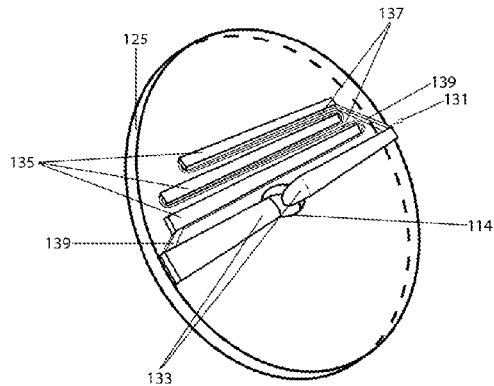
Fig. 1e
Fig. 1f

BODILY COOLING FLUID TECHNIQUES

FIELD OF THE INVENTION

The present invention relates to the field of athletic apparel, supplements and equipment.

BACKGROUND

Animals generate heat during physical exertion, which can lead to a detrimental escalation in body temperature. To regulate that escalation, human beings, unlike some other animals bearing fur, perspire during exercise. Their perspiration then may evaporate from bare skin and thereby aid in cooling the body. This form of sweat is known as eccrine perspiration, and involves the eccrine sweat glands, which are distributed throughout the skin surface of the body. Thermoregulatory sweat from eccrine sweat glands includes water and Sodium Chloride (common table salt), which may be, to some degree, reabsorbed by the body to decrease salt loss.

In modern athletics, hyperthermia during intense competition is a serious issue, both in terms of health and athletic performance. Although natural thermoregulatory sweating may be helpful in controlling overheating, it may be ineffective, or insufficiently effective, for a variety of reasons. The exercise environment may be too hot and/or too humid to permit effective evaporative cooling by sweat. The athlete may even become uncomfortable with the dampness of his or her own body, and his or her garments saturated with sweat, and "towel off" or change clothing during exercise. Conversely, some athletes, particularly in marathon running, may not mind the damp sensation, and in fact douse themselves with water in an effort to cool down more greatly than with their own sweat, alone, because the water may be temporarily cooler than the athlete's sweat. However, this added relief may be temporary, and may come with the disadvantages of sodium and other electrolyte loss as those agents are washed from the body, closing eccrine sweat glands, and other factors causing decreased sweating efficacy.

Some freezable gels have been created in pads that aid in locally cooling painful or injured parts of an athlete's body. These pads may include compression bands, to further reduce swelling. These pads tend to reduce or restrict cooling by sweat, because sweat and other glands and pores may be closed by lower temperatures. Some "cooling" gels have been brought to market that provide a cooling sensation for post-exercise pain relief. Typically these formulations include menthol. The U.S. government, and other entities, have created artificial sweat formulations, which closely mimic the composition of eccrine sweat, for the purpose of in vitro or other product testing.

In recent decades, progress has been made in fundamental research concerning the thermal topography of the human body and the distribution of eccrine sweating during exercise. In *The topography of eccrine sweating in humans during exercise*, Cotter J D, Patterson M J, Taylor N A, Eur. J. Appl. Physiol. 71(6):549-54 (1995), the authors reported steady state sweat rates of men during stressful exercise (cycling) and heat exposure. The scapula, forearms, hands, stomach and lower back sweat rates were relatively great (and are listed here in descending order) and exceeded sweat rates for the chest, upper arms, calves and thighs. The authors noted that their results differed from measurements of sweat response taken during resting heat stress, with a subject laying in the supine position. In that scenario, sweat onset in a caudal-to-rostral pattern, whereas in the author's work, onset was similar across most regions. Other research has indicated that there are some important differences between the sexes in regional sweating rates. For example, sweating rates are relatively low at the breasts in aerobically trained, exercising female subjects, when compared to aerobically trained, exercising males. In addition, sweating rates were relatively great in the arms and hands of females, in comparison to males. But upper back regional sweating was relatively great in both sexes. See Smith C J, Havenith, G, *Body Mapping of Sweating Patterns in Athletes*, Med. Sci. Sports Exerc., 44(12):2350-2361 (2012). Still other research has revealed thermal images for athletes prior to exercise, upon reaching age-predicted maximal heart rate, and during recovery from exercise. This work shows a tendency for relatively great cooling effects in the thighs, forearms and torso of trained male participants. See *Thermal Imaging of Cutaneous Temperature Modifications*, Merla A, Mattei P A, Di Donato L, and Romani G L, Annals of Biomed. Engineering, Vol. 38, No. 1 (Jan. 2010).

It is the inventor's new, working hypothesis that a variety of specific factors contribute to a cooling adaptation response by humans, partly exhibited in the results of the research discussed above. First, the effective thermal exchange rate for net body cooling differs at different skin regions of the body. Areas lined with adipose tissue, or with other forms of insulation, and without thermal communication to relatively great blood flow are less effectively used by the body as a cooling surface. As a result, the human body makes less investment in a cooling apparatus in those areas, and some of those areas may be thought of as bearing a thermoregulatory "penalty" in the sense that temperature regulation efforts (such as sweating) bear a cost too great to be justified (such as simple loss of water and electrolytes, without significant enough cooling) in comparison to other skin areas. In addition, skin regions of the body with high local blood flow and low local underlying body volume are more effective for heat transfer (and, therefore, as a thermal regulation device) due to the cube of a length relating to volume of an object and square relating to surface area of an object principle of engineering, biology and physics, generally ("cube-square law"). Overall, the effect of gravity pulling sweat, as a cooling fluid, from one region to another as it evaporates changes the ideal distribution of sweat gland activity upon exercise, in comparison to what it would be in different (e.g., supine) positions or in a gravity-free environment. Other factors, such as the diffusion characteristics of the surface of skin in each region, or the flow of fluid through fabrics, and the present conformation of the skin and fabrics, the characteristics of a distributed cooling fluid or matrix, as well as atmospheric and other conditions, also may modify the ideal distribution patterns of a cooling fluid. The principles of this hypothesis, its refinements, and others which have followed and may come, may impact some, but not all, of the design factors set forth in this application.

It should be understood that the disclosures in this application related to the background of the invention, such as those in, but not limited to those in, this "background" section, do not necessarily set forth prior art or other known aspects exclusively, and may instead include art that was invented concurrently or after the present inventions and details of the inventor's own discoveries and work and work results. Thus, nothing in this background section should be construed as an admission of "Prior Art." It should also be understood that, for convenience and readability, this application may set forth particular pronouns and other linguistic qualifiers of various specific gender and number, but, where this occurs, all other logically possible gender and number alternatives should also be read in as both conjunctive and alternative statements, as if equally, separately set forth therein.

SUMMARY OF THE INVENTION

New personal and athletic cooling techniques are provided. In some aspects of the present invention, a new rapidly-evaporating (and/or, or partly, sublimating) cooling liquid, gel, movable medium or fluid ("fluid") is sprayed, doused or otherwise distributed over or about an athlete's body, and/or worn garment(s), in thermal-reduction-optimized gravitational and movement-induced patterns, to maximize cooling during exercise. In some aspects, a garment may serve as the matrix or platform for this distribution of the rapidly evaporating (a.k.a. "volatile") fluid. In other aspects, the matrix may be separate from the garment, but may be associated with it, and separable. Tuned, heat-absorbing port-defining rings coupled with closable, elastomeric internal ports may cause the release of the cooling gel or fluid upon local underlying body heat, or other regional heat, exceeding a threshold, and resealing (halting release) upon body heat dropping below a threshold.

In still other aspects, heat-absorbing expanding or conformation-changing sub-elements of a heat-absorbing and exchange element rise away from the location of heat absorption (near a user's skin) toward a wider containing region for heat release, while other freshly heat-liberated (cooled down and shrunk) elements then descend and exchange places with the larger sub-elements, to absorb more body heat.

Preferred Formulations

Although any relatively volatile fluid, liquid or other substance (including pure elements, compounds and mixtures) that are safe for contact with human skin may be used, preferably, the formulation for the evaporative cooling gel will include water and a lower proportion of isopropanol and/or ethyl alcohol (relative to the water component). In some embodiments, safe, highly-volatile agents may be included for separate deployment to create a more immediate cooling effect, prior to the evaporative cooling of water and ethyl alcohol.

Ethyl alcohol itself is more volatile than water and could be used to provide some staged cooling in combination with water already. However, preferably, in staged or single administration formulation, the proportion and/or amount of alcohol is low enough to avoid any significant irritation or other adverse health effects for at least a majority of users due to the alcohol, while still of a sufficient proportion to provide a more rapid evaporative cooling prior to the onset of substantial evaporative cooling from the water component, and creating a smooth transition between the evaporative cooling due to each component. Any of the components of the cooling fluid formulation may be stratified or separated (for example, by weight, low-dissolution profiles of neighboring stage/layers, or by separate storage vessels), to avoid a single cooling profile and instead provide staged cooling.

Also preferably, a safe, volatile emollient and/or spreading agent may be included, such as Decamethylcyclopentasiloxane ("D5"), such that additional evaporative cooling may be supported while aiding in the distribution of the fluid and preventing irritation, and producing a generally "silky" and cool, yet drier feel for a user of the fluid. D5 may also bear the side-benefit of safe use with clothing, and, in fact, sequestering dirt or other staining agents that might be present on the user's skin, clothing, or within the remainder of the formulation. Alternatively, or in addition, a different soothing agent may be used. Where oily or other hydrophobic agents are used, the formulation may also comprise an emulgent to create an emulsion that may be accessed and washed away with water. Further, an emulsion stabilizer, such as cetearyl alcohol, may be included.

To reduce flammability of flammable components (if used), a safe flame retardant may be added in the formulation as well. Such a component may be of particular usefulness in the context of firefighters, racecar drivers, and other high-exertion activities that may include the risk of fire, but nonetheless warrant use of the cooling fluid.

In addition, a component or agent for inducing vasodilation and/or sweat gland pore dilation may be included, to increase heat exchange and/or water and electrolyte flow to and from the user's skin. That component (e.g., as in the use of menthol) or a separate component may also aid in increasing the user's comfort by acting as an analgesic and/or activating "cool" heat nerve receptors—enhancing the user's sensation of cooling, and decreasing irritation due to overheating. To avoid other inflammatory responses with certain vasodilators, a selective anti-inflammatory response agent, such as thyme oil, may also be used.

A lubricant may also be added to aid in reducing irritation, and may include anti microbial activity, as with Shark Liver Oil. A phenol, such as methyl salicylate, if used, may also be used as an analgesic, or a separate analgesic may be used.

A decongestant may be added to ease the athlete's breathing during exertion, such as Eucalyptol.

Also preferably, the formulation may include a preservative and/or anti-microbial agent, or, alternatively or in addition, an antimicrobial agent and/or structure may be provided within or in the structure of the distribution system, options for which discussed in greater detail below.

If water is used in the formulation, preferably, de-ionized water is used to lower the boiling point and increase evaporative cooling at lower temperatures. However, in some aspects, electrolytes may be included to aid in "salting" the user's skin to aid in coverage and replenishing lost salt reserves. Other components/agents may also be added to salt, lubricate or otherwise enrich, enhance or add nutrients to the skin and improve its performance in athletic endeavors. Any lubricant component or agent used may be water-based, hydrophilic and/or more volatile than water, to further enhance evaporative cooling. But other lubricating components or agents may also, or alternatively, be used.

Also preferably, a sequestration or chelating agent and/or filtration medium may be included to increase the purity (and therefore potential vaporization) of a more pure water product while also removing enzymatic metals and other impurities in the gel, increasing its storage stability, and decreasing negative impact of the gel on garments and/or the user's skin. Any chelating agent proven safe for skin contact and environmental impact may be used, including but not limited to EDTA (Ethylenediaminetetraacetic acid) or EDDS (Ethylenediamine-N,N'-disuccinic acid). If EDTA is used, it may be used in its disodium or tetrasodium salt, to increase its solubility in the formulation.

Compressed gas(es), such as air, may be administered with the formulation and, along with the flow dynamics of the housing of the fluid formulation, or channels, may encourage cooling of both the fluid and the user's body upon release onto a region of the user's body due to the effect of lowering temperatures caused by released expanding gasses—compared with their temperature prior to release and expansion. Flow dynamics may also create low pressure areas in ideal locations (near a user's body, in regions where cooling is desired). A dissolved gas may also be used within the formulation to increase its volatility and increase the cooling effect of the cooling fluid. Preferably, such a gas is substantially harmless for a user in contact with it in accordance with aspects of the present invention—such as with inert, noble gasses. Such dissolved gasses may also be used to encourage coolant purity, discouraging the dissolution of competing impurities.

A surfactant, such as a soap, may be used, preferably in trace amounts, to decrease surface tension with impurities and components of the formulation.

Preferred aspects of a formulation for a coolant fluid are set forth in this application. However, the formulation description above is exemplary only, and innumerable safe, volatile formulation component(s) may be substituted in some aspects of the present invention. For example, and by way of example only, water alone may be used in conjunction with the coolant fluid distribution systems discussed in greater detail below. In general, the formulation (as well as the deployment matrix and garments in which they are seated or with which they are associated) may be modified in the selection of components, the amounts of each component, and all other relevant factors, depending on relevant factors for use—such as, but not limited to, factors related to the environment for use and nature of use. For example, a formulation may be less volatile, and slower-acting, and the matrix may (or constituent vessel walls) may be freer-flowing, in less humid environments with low air pressure, higher temperature and where longer effective deployment is preferred, such as in use during a marathon.

BRIEF DESCRIPTION OF THE DRAWINGS

FIGS. 1a-1j are enlarged depictions of several alternative embodiments for coolant-releasing ports comprised within the matrix of FIG. 1, and which may also be used in other coolant-deploying matrices discussed throughout this application.

DETAILED DESCRIPTION OF THE INVENTION

Figure 1:
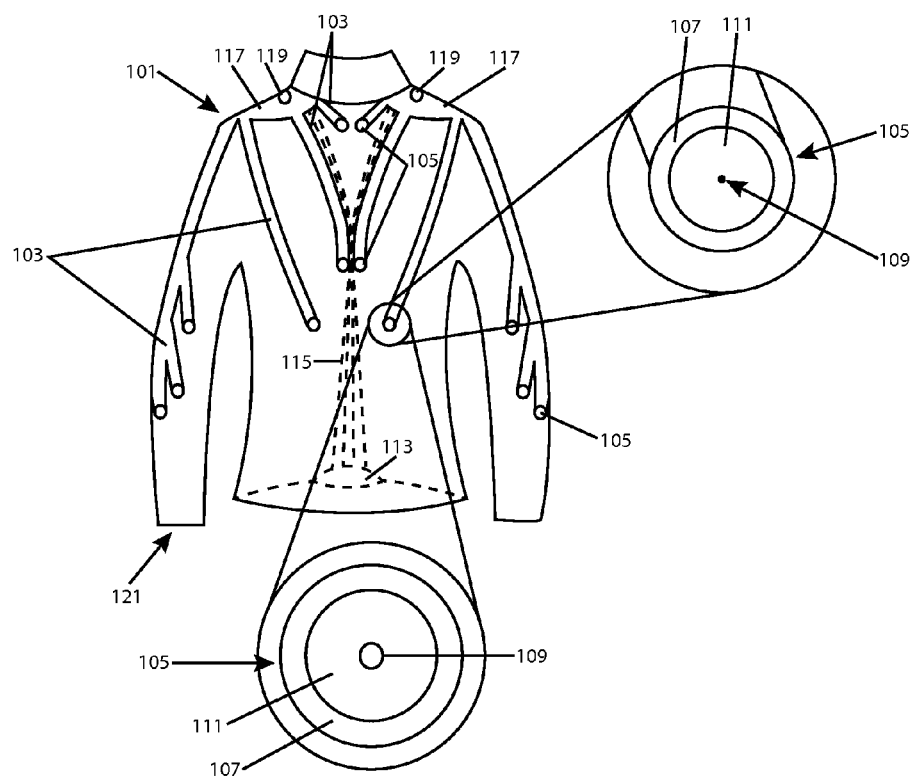
FIG. 1 is a front view of a long-sleeved athletic garment for a female athlete, associated with or comprising ("associated with") a variable coolant deployment matrix, in accordance with aspects of the present invention.

FIG. 1 is a front view of a long-sleeved athletic garment 121 associated with an exemplary variable coolant deployment matrix 101, in accordance with aspects of the present invention. A coolant fluid, gel, powder, solid(s), powder, fabric, gas or liquid formulation (or any mixture thereof), such as that with ingredients and preparation discussed in the remainder of this application ("coolant," "fluid," "coolant fluid" or "cooling fluid"), may be guided and variably-released by matrix 101. The matrix 101 may comprise open or variably opening/closing and or coolant-transporting, -releasing or -passing channels, pathways or tubes ("conduits" or "channels"), such as those pictured as conduit examples 103. Conduits 103 may terminate at variable ports, such as those pictured as exemplary ports 105. Ports 105 may release coolant upon detecting, or a control system and/or user detecting, a need to cool a user's body as a whole (about which the matrix is mounted) or in the locations at or about, in a diffusion path of fluid flowing from, and/or gravitationally running beneath, said ports. If general body or local overheating, or a trend toward such overheating and/or potential overheating, is detected by body temperature sensors and a connected (e.g., computer) system, ports such as those pictured as 105 may open to release some coolant, and even different grades, types, amounts or locations thereof depending on a wide variety of cooling and optimization factors, discussed in this application. Alternatively, however, and preferably in the instance of use by athletes, such as those running in a marathon, an auxiliary control system with computers and sensors are not used, in order to reduce weight, and, instead, ports 105 automatically open to a variable degree depending on local, regional temperature changes. Also preferably, a temperature-expanding port, such as that variably pictured in zoom window FIGS. 1a and 1b, is used. More preferably, a temperature-expanding ring, such as the example shown as 107, may be used to define a variably coolant-releasing port hole 109. The temperature-expanding ring 107 is preferably comprised of a relatively light metal that expands relatively greatly with heat, such as aluminum or silver, or alloys including them, or may be made of an elastomeric housing filled with a fluid with even greater thermally-expanding properties, such as alcohol or water, or mixtures including them. If so, the coolant itself may be permitted to expand and create that port-hole widening or opening pressure, preferably with a one-way valved communication between the space in the ring 107 and the insides of the conduits, permitting expandable coolant to fill, but not exit the port holes except through an inner opening, closed when the port hole 109 is closed. Even more preferably, however, an elastomeric inner ring(s) 111 is attached to expanding material ring 107 and, at the athlete's resting body temperature, and a margin above that may be variably selected by a user and/or system, and regionally so selected, substantially holds closed port hole 109. Two or more variable-width and/or -location circumferences of inner ring(s) 111 may also create a complete seal when outer ring 107 is adequately cool, but open a coolant releasing hole ("port") when adequately warmed. Such alternatives are shown in greater detail in FIGS. 1c-1e. But, alternatively, a substantially-closed hole 109 prior to heating can be achieved with adequately tight elastomeric materials, without a multi-layered design, and, instead, a single layer, as specifically demonstrated in the examples provided in FIGS. 1*a*, 1*b* and 1*f*, may be used.

In Zoom FIG. 1*a*, rings 107 and 111 are shown in a cooled condition, with variable coolant-releasing hole 109 substantially closed. In this condition, preferably, the pressure from the weight and other acceleration of coolant fluid maximally filling coolant matrix 101 is insufficient to force coolant out of hole 109. However, in some embodiments, a heat expanding ring 107 may not be used and additional pressure from, for example, a user control, such as a pressure increasing hand-actuated air compression bulb, such as the example shown as 113, may be used to drive coolant out of hole 109, even when it is in this substantially closed condition. In more detail, such a pressure bulb, when pumped by a user's hand, may drive air through pressurizing tubes 115, into coolant reservoir sources 117, which may be variably filled by a user through closable filling ports 119. In some designs, different or separate bulbs (or other actuators) with different or separate air tubes going to different or separate reservoir sources, with different or separate fluid types, target regions, and with other variable techniques for use in response to different or separate, discussed in this application, may be differently or separately actuable by the user. Pressurizing tubes 115 may be maintained coolant free by way of a one-way air valve, permitting pumped air to enter reservoir sources 117 without back-flow into tubes 115. In another embodiment, the act of donning the garment and/or matrix (or other actuation command or gesture, whether intended as such or not) may itself trigger the onset of release, or a process leading to release or potential release, of coolant fluid from the matrix—but before donning, the matrix will not deploy coolant fluid. For example, the stretching associated with donning the garment and/or matrix may pull open valves allowing the release of the fluid.

Proceeding to FIG. 1*b*, the rings 107 and 111 are depicted in a thermally-expanded condition, and a resulting enlargement of hole 109 is shown, which, under some circumstances, permits some coolant to escape and cool the surrounding area, areas gravitationally beneath it, and other areas in the diffusion flow path or force path of the fluid, other flow conditions permitting. As this regional cooling occurs, the rings themselves may become cooler and close hole 109, returning it to the cooled position. In this sense, the rings 107 and 111, and matrix 101 as a whole, may operate by self-regulation and feedback. Preferably, rings 107 and/or 111 sufficiently open hole 109 upon body and local regional heating corresponding with physical exertion and physical exertion, or (in some embodiments) other heat stress, and, even more preferably, with such heating or heating patterns which may indicate a need for auxiliary cooling (not adequately performed by the body's own thermoregulatory systems). However, a control system may instead match patterns of regional and/or whole body temperature changes that match such a thermal condition. In this sense, the system may serve as a safety net preventing heat stroke or shock, or other conditions where the body is unable to cool itself sufficiently. But more reactive and proactive temperature response(s), and comfort-enhancing responses, may also, or separately, be implemented by the matrix, and tiered reservoirs with different release conditions, timing of release or location of release, which may include different amounts or types of coolants, may also or alternatively be used to both ease a user's comfort and prevent injury, as actuated by the control system (which may include actions, commands and selections by a user for each of those purposes). In some aspects of the present invention, a regulatory system (which may or may not permit manual coolant control and system settings input by a user, depending on the exact embodiment) may also or alternatively be used, which senses such heating and patterns sub-regionally, and/or as a whole, identifying body heating, body heating in different regions/depths of the human body, as well as ambient heating conditions (and patterns thereof) and matches those heat conditions and patterns to corresponding needs for auxiliary cooling by the matrix which is then implemented. Such alternative embodiments may, for example, be carried out by an array of sensors and coolant-releasing servo/motors and a control system, such as a computer control system, in communication with such sensors and servo/motors.

As mentioned above, FIGS. 1*a*-1*i* depict different options for port-defining, opening and closing ring(s) (such as 111) (ring devices for variably controlling the outflow of cooling fluid). In FIG. 1*c*, multiple rings/layers, 123 and 125, each include one hole, 108 and 109, which, as pictured, in a relatively cooled condition, do not overlap and are next to one another. As in each of FIGS. 1*a*-1*i*, rings/layers 123 and 125 in FIG. 1*c*, or at least one of them, may be attached to a thermally-expandable outer ring or other structural device (not pictured), either separately or together, preferably by their outer edges. As that outer ring or other device (not pictured) attached to the rings/layers 123 and 125 expands, one of or each hole 108 and/or 109 also expands and, at the temperature causing the expansion, those holes begin to overlap with one another. That overlapping and open condition is shown in FIG. 1*d*. As a result, and as shown by fluid pressure/flow arrows 127 and 128, coolant is not able to flow through the cooled set of rings shown in FIG. 1*c*, because they are pressed tightly together and their holes do not overlap laterally, but coolant is able to flow out through the rings in the condition pictured in FIG. 1*d*, where their holes do then overlap.

A number of other controllably variably-sealing and -overlapping layered shapes may alternatively be used for coolant-releasing ports, as long as they permit the controlled release and/or distribution of coolant fluid. For example, in FIG. 1*e*, a symmetrically-held blocking piece 129 may be used to variably fully hold closed the coolant release port, the top surface of which is shown as 110, in an inner elastomeric ring layer. Surrounding hole notches, shown as 112, in a more distal layer of the port, which may contain the blocking piece 129, may variably permit the release of coolant with expansion of the ring 125.

FIG. 1*f* presents a technique for increasing the expansion-to-temperature-increase ratio of a port-hole-expanding material or device. Such increased ratios may be desirable to program or "dial in" expansion causing coolant release to particular temperature levels, differences or other thermal patterns, as may be desirable in a particular matrix 101 for a particular user and/or activity environment. Among other things FIG. 1*f* demonstrates that port holes, such as those shown as 109, 110 and now 114, may be expanded and/or contracted with other configurations of expanding materials and/or devices, other than with an outer expanding and attached ring, discussed previously. A lateral expansion- and/or contraction-causing sub-system 131, comprising structural member components, is attached to or further comprises retraction lips 133, which may be inserted into, and exert outward opening force against, a port hole 114, as pictured. The expansion- and/or contraction-causing system 131 may include expanding bars, such as those examples pictured as 135, which, as with the expansive outer rings discussed above, expand with increasing heat (thermally expand). However, in the instance of system 131, the expansive effect on the pore is greatly increased in comparison to a ring configuration of the same diameter/width, because each expanding bar 135 is attached to a neighboring bar 135 in an additive manner (e.g., right-hand side of the bar 135 closest to the port hole 114 attached to the left-hand side of the next expanding bar outward, and so on). To avoid subtraction from this additive effect, the structural pieces used for these additive connections, such as those examples pictured as 137, are composed of a substance that is far less expansive, or that may not thermally expand at all, or that even contracts with increasing heat to increase the additive effect. Final drive connectors, such as those pictured as 139, also may be of a more thermally expansive material, if the structural configuration chosen benefits from the expansion. The overall system 131 of the device need not be unilateral (on one side of the ring 125 or one side of the port 114) although it is pictured that way for ease of illustration, and in some embodiments, a multilateral device may be preferred for self-regulation of the port, for ease in designing predictable reaction patterns and for increased reliability. Also although not pictured for simplicity, guides or lateral (roughly upward or downward on the page in the figure) expansion preventers may be used to ensure that more thermal expansion of the expanding bars 135 and movement of the lips 133 translates more predominantly into expansion of port 114—as opposed to lateral flex of the system 131 and/or its joints.

Figure 1G:
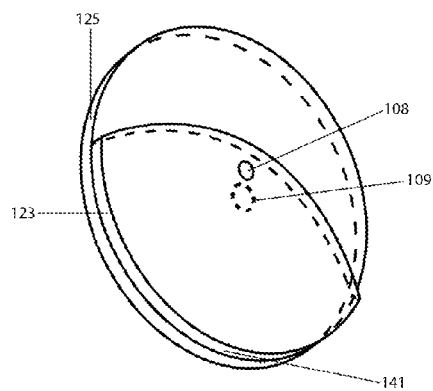

FIG. 1g illustrates a multiple-layered, multiple-hole embodiment similar to that pictured in FIGS. 1c and 1d, except that thermal expansion of a thermally expanding attached outer ring or device (again, not pictured) results predominantly in the shifting of one of the two port holes, 108, rather than in expanding it, such that, when thermally expanded, that outer ring or device draws hole 108 over the inner hole 109, allowing the release of fluid, but need not substantially expand hole 108. To accomplish this, one of the inner ring layers, 123, is only partially attached to the thermally expanding outer ring/device—namely, at the edge/side for attachment shown as 141. As an alternative, though not preferred, other connections, including a pushing connection, between layer 123 and the expanding ring or device, may be used. Preferably, the inner port hole (the surface of which is shown as 109) (or outer port hole, in a reverse configuration, in which the inner layer is designed as the outer is in this figure) is slightly larger than the port hole that is drawn across it with temperature increases, to allow for some margin of error in alignment, especially as the system 101 ages and is worn in.

Figure 1H:
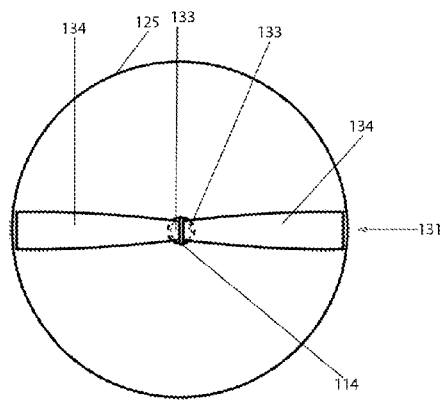
Figure 1I:
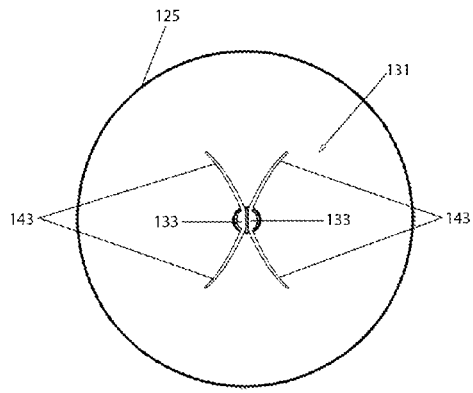

In FIGS. 1h and 1i, some variable embodiments for port-closing and -opening lips 133 (and their lip/retractor slidable outer pieces 134) are shown. FIGS. 1h and 1i show the outer and inner surface, respectively, of part of the thermally-expanding port system 131, in a thermally-cooled (closed) condition. The lips 133 are shown fully inserted into, and substantially closing, port 114. As shown, the shapes of lips 133 are complementary to one another such that, as they converge (as pictured) they form a seal that prevents fluid from escaping port 114. To aid in creating a closed seal, lips 133 may also be partly (and preferably, at their outer surface) composed of an elastomeric or other seal-encouraging, semi-flexible material and/or overlapping shape, also aiding in maintaining that seal. The lips also may be contoured to match, comprise an elastomeric component and form a substantial seal with, the outer edges of port hole 114. Part of the lips, or flanges, 143 on the inner side shown in FIG. 1i, may also grip and hold the inner surface ring layer 125. Preferably, those flanges 143 have outer surfaces that curve both toward insertion into port hole 114 and against the direction of compression of layer 125, to discourage slippage of lips 133 from hole 114, under expansion resistant pressure. These lips, if sufficiently broad, will also discourage folding and folding escape of layer 125 when under that pressure.

Figure 1J:
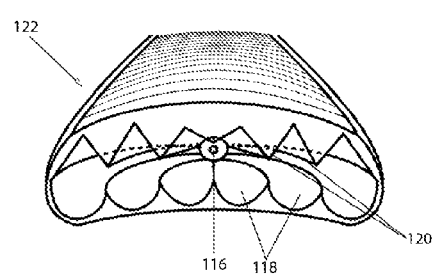

FIG. 1j illustrates a perspective of another coolant release port—this time with water flow and/or droplet division structures augmenting its outer and/or flow-directing surfaces. To encourage the spread of coolant fluid variably released from a port hole, now shown as 116, upper and lower guide walls 118 and 120 section the volume occupied by any emerging coolant flow, and even individual droplets, and separate and channel it/them to different sub-regions or channels of the matrix, garment and human body, diffusing it/them to selected areas for preferred coolant locations, diffusion and coverage. The upper and lower division structures (e.g., tapered walls, as pictured) 118 and 120 may completely close against one another or be more open, as pictured, (or may be user or system variable between the two) to maximize diffusion at particular flow rates of coolant fluid. Alternatively, to exploit the colligative nature of water and other fluids, particularly on smaller scales, the upper and lower divisions may begin as somewhat separated, and then draw closer together or even meet upon exit, to force a more even division of the emerging fluid/droplet(s). In the figure, the perspective is shown from the bottom and outer sides of the end of a coolant tube terminus 122.

As pictured in FIG. 1, matrix 101 may be a part of and/or embedded within, or otherwise associated with (either permanently or dynamically) a garment or other structural scaffold, such as the long-sleeved shirt 121 pictured. In the example provided, the shirt 121 and associated coolant matrix 101 is designed for a trained female human athlete, in good cardiovascular condition. Overall, in FIG. 1, the distribution of coolant-releasing ports 105 are demonstrated in an array that is complementary to the cooling needs of such a user under exertion and/or heat stress. The ports release at and above regions demonstrated by research, in the inventor's opinion, to be consistent with, or potentially consistent with, the body's most effective regions for transpiration cooling. For example, research has shown that sweat response and cooling may be particularly preferred at the forearm of such a woman. As a result, several channels and ports terminate, and empty, onto or above, and diffuse throughout, the forearm region. As another example, research may support, and the inventor's assessment is, that a coolant response is less useful or optimal about such a woman's breast tissue. As a result the coolant channels and ports, and resulting coolant release and gravitational and osmotic or other diffusion flow pattern, substantially circumnavigate the breast areas in the garment 121. This, and other optimization patterns, may also be accomplished or urged with the preferential use of garment materials with more osmotic or surface tension in areas drawing the coolant in similar patterns, and such pathways or channels, in some embodiments, may not include tubes or ports, such as those discussed above. Rather, the pathways in the garment itself may serve as the matrix for preferred coolant flow. Also, particular fabric patterns and components may be used to maximize thermoregulatory evaporation and/or conduction of heat to create contact cooling for the user's body. Such patterns will be discussed in greater detail below, with reference to FIG. 10.

Figure 2:
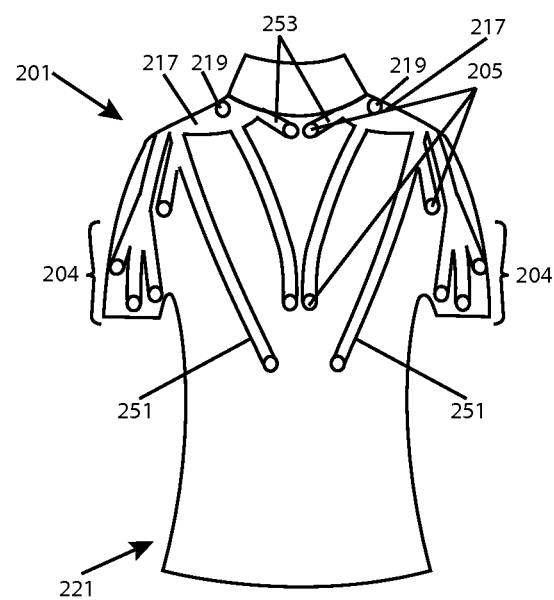
FIG. 2 is a front view of a short-sleeved athletic garment for a female athlete, associated with a variable coolant deployment matrix similar to that depicted in FIG. 1, but optimized for deployment from a short-sleeved garment.

FIG. 2 is another front view, depicting a simplified coolant-channeling matrix pattern 201, this time for a short-sleeved athletic garment 221, but again for a trained female athlete. The variable coolant deployment matrix 201 is similar to that depicted in FIG. 1, but optimized for deployment from/within a short-sleeved garment. For example, because the channels and ports would be cumbersome and irritating if extended beyond the short sleeves to cool the forearms more greatly, a more heavy distribution of coolant-releasing ports 205 are shown in region 204, near the edges of the sleeves, but not extending substantially beyond the edges of the sleeves. However, as with the matrix depicted in FIG. 1, coolant will run generally downward with gravity and, due to the normal shape of a trained female arm and diffusion and arm swinging, will run to the optimal cooling forearm regions. In some embodiments, however, which may be preferred for some objectives, the channels and/or coolant-releasing ports, as may be applicable in the particular embodiment, may extend to some degree beyond the edges of the sleeves to ensure optimal direction and diffusion of the coolant. Also, in some embodiments, such channels and/or coolant-releasing ports may extend to the edge of the sleeves, to prevent the broadening distribution of coolant partially absorbed and redistributed by gravity and arm/body movement, although, in some applications, that redistribution itself is preferred—for example, where the distribution, due to the coolant formulation and exercise and ambient conditions, may be more effective with that distribution.

Other matrix-optimizing adjustments to the distribution of coolant channels have also been carried out in FIG. 2. For example, channels 251 and 253 are each slightly closer together, away from the sleeves, in FIG. 2 than in the instance of analogous channels pictured in FIG. 1. These slight adjustments may be more optimal than that pictured previously, assuming the same coolant formulation is used, to strike a balance between cooling evaporation and migration through the channels, matrix and garment, to contact and cover optimal areas of the user's body before performing evaporative cooling, and other aspects of the coolant formulation and other conditions.

It bears repeating that the embodiments specifically discussed thus far address some potentially optimal coolant distributions for trained female athletes. However, different distributions may be optimal for different human phenotypes, in different training conditions and in different environments, under different thermal and other stresses, and with different distributions of fat, muscle, vasculature and other conductive and insulating tissues of the person. In various embodiments, such optimizations in design and deployment may be variably selected by a control system, the user, or may be pre-set in particular garments and/or matrices designated for such particulars.

Figure 3:
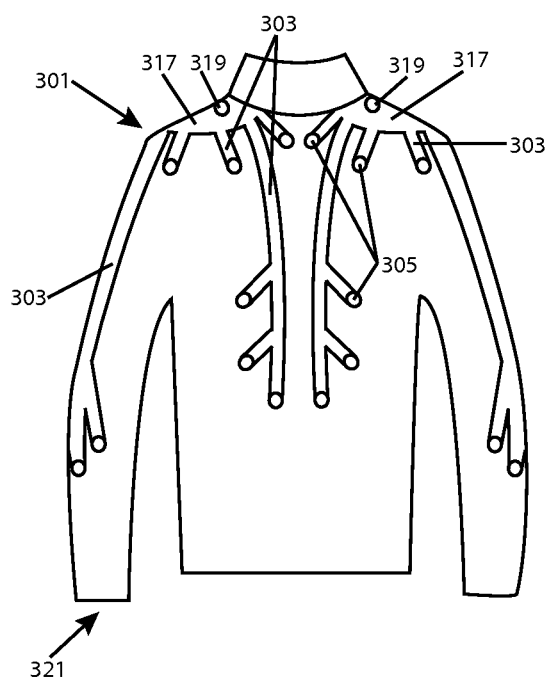
FIG. 3 illustrates a different coolant deployment matrix associated with another long-sleeved athletic garment, in which the matrix is instead optimized for a trained male athlete.

As another example, FIG. 3 illustrates a different coolant deployment matrix, 301, within another long-sleeved athletic garment, but in which the matrix 301 is instead optimized for a trained male athlete. As with FIG. 1, above, FIG. 3 is an exemplary front view of the long-sleeved athletic garment and matrix. Based on the inventor's hypotheses and observations and data concerning which body surface regions are most effective when treated with a coolant fluid (and, in particular, an evaporative coolant fluid) the matrix 301 has been optimized in a way to introduce more coolant fluid on or about those regions, efficiently, in the context of all relevant factors. As discussed above, those factors include, among other things, channel and garment characteristics, gravity, the athlete's phenotype and training condition, skin diffusion and exertion and/or heat stress environment. One way that the distribution may be differently optimized is by changing deployment regions, amounts, timing and types and types of coolant fluid deployed, for example, by relocating ports and establishing orders, times, amounts, patterns, sequences and durations of coolant fluid deployments (which may be of different fluids, and tiered in delivery). Other forms of optimization of distribution, for example, discussed elsewhere in this application, relate to selection of the types of available fluids by the user and/or system.

As with the matrix discussed with respect to FIG. 1, a wide variety of differing port designs may be, alternatively or concurrently, used at the cooling tube terminal ports 305 of conduits 303 within matrix 301. Examples of such alternative embodiments are discussed above, with respect to FIGS. 1*a*-1*j*.

To note a few of the differences in the optimized matrix pattern shown in FIG. 3, as compared to FIG. 1: The matrix pattern of FIG. 3 provides greater coverage of the chest and, in particular, the upper chest/pectoral region of the user, than the matrix shown in FIG. 1. This is because data and the inventor's research demonstrates that less insulating material is present in a trained male athlete in those regions and, therefore, cutaneous cooling conduction to the blood stream is greater for the male athlete, as compared to a female athlete. As a second example, the forearm regions of the matrix, while still provided with coolant fluid coverage, have less coverage than when compared to FIG. 1. Again, this reflects data and the inventor's research indicating that female athletes benefit more greatly from emphasized cooling in those regions. These differences are illustrative, but not exhaustive, of the infinite variations and optimization patterns that may, alternatively or in addition, be used to optimize a matrix, garment and bodily cooling matrix, within the scope of the present invention. Any data, hypotheses or know-how and experience concerning any component, the environment, or user's body to be conditioned by the invention may be used to further optimize the matrix/garment and performance of the coolant fluid.

Figure 4:
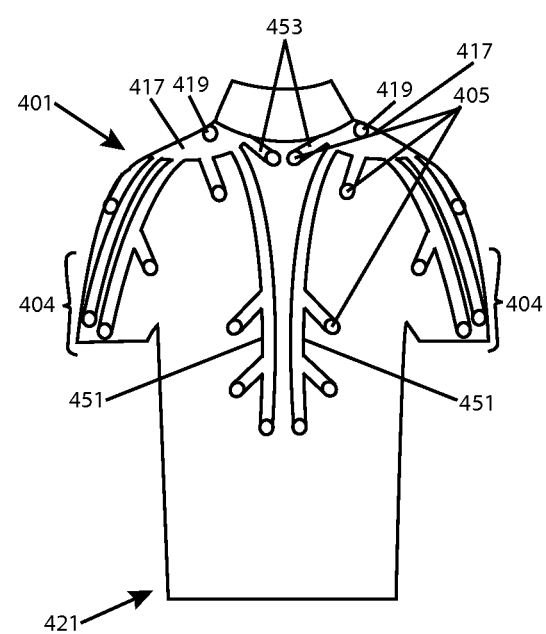
FIG. 4 is a front view of a short-sleeved athletic garment for a male athlete, associated with a variable coolant deployment matrix similar to that depicted in FIG. 3, but optimized for deployment from a short-sleeved garment.

Similar to FIG. 2, FIG. 4 is another front view depicting a simplified coolant-channeling matrix pattern 401 for a short-sleeved athletic garment 421, but this time for a trained male athlete. The variable coolant deployment matrix 401 is similar to that depicted in FIG. 3, but optimized for deployment from a short-sleeved garment. For example, because the channels and ports would be cumbersome and irritating if extended beyond the short sleeves to cool the forearms more greatly, a more heavy distribution of coolant-releasing ports 405 are shown in region 404, near the edges of the sleeves, but not extending substantially beyond the edges of the sleeves. However, as with the matrix depicted in FIG. 3, coolant will run generally downward with gravity and, due to the normal shape of a trained male arm, will run to the optimal cooling forearm regions. As discussed with reference to FIG. 2, above, in some embodiments, which may be preferred for some objectives, the channels and/or coolant-releasing ports, as may be applicable in the particular embodiment, may extend to some degree beyond the edges of the sleeves to ensure optimal direction of the coolant. Also, in some embodiments, such channels and/or coolant-releasing ports may extend to the edge of the sleeves, to prevent the broadening distribution of coolant partially absorbed and redistributed by gravity and arm/body movement, although, in some applications, that redistribution itself is preferred—for example, where the distribution, due to the coolant formulation and exercise and ambient conditions, may be more effective with that distribution.

Figure 5:
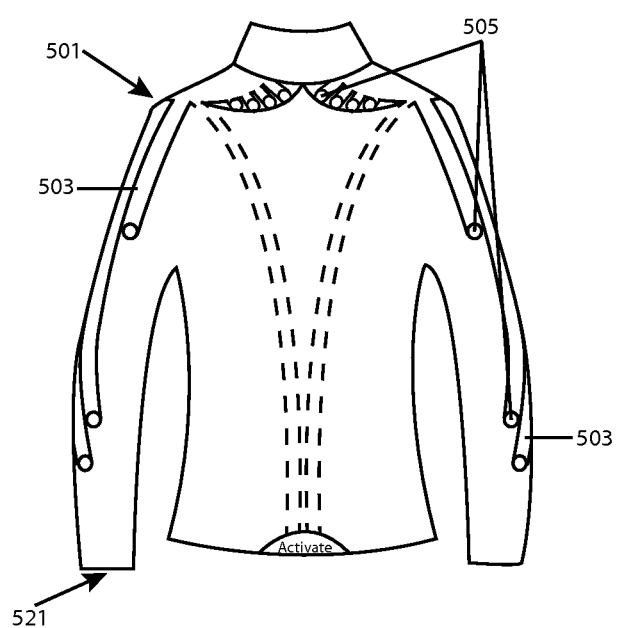
FIG. 5 is a rear view of the long-sleeved athletic garment associated with a variable coolant deployment matrix previously illustrated in FIG. 1.

Again as discussed above, other matrix-optimizing adjustments to the distribution of coolant channels have also been carried out in this figure concerning a short-sleeved variation for the same type of athlete. For example, channels 451 and 453 are each slightly closer together, away from the sleeves, in FIG. 2 than in the instance of analogous channels pictured in FIG. 1. Such adjustments and differences are more optimi- FIG. 5 is a rear view of the long-sleeved athletic garment associated with a variable coolant deployment matrix previously illustrated in FIG. 1. The distribution of variably opening and or coolant-releasing, -channeling or -passing conduits, such as the examples shown as 503, and ports, examples of which are shown as 505, from the rear view, exhibit an exemplary optimized distribution throughout the garment, but now for the rear of the garment and user's body, as well as other factors discussed previously. Once again, the garment's user is taken to be a trained female athlete, data for which indicates that the upper back is an optimal cooling region during heating due to exertion. Accordingly, a high concentration of conduits and ports are present in the upper-back region, and above that region, such that gravitational, osmotic and other force-driven flow may provide an effective coverage in that ideal region with coolant fluid. Additional flow of coolant fluid may ultimately reach lower, wider-spread regions of the user's back, but the location(s), degree(s) and type(s) of that coverage will depend on the exact evaporative cooling and thermodynamic profile of the fluid formulation chosen, as well as garment characteristics, exact user characteristics and environmental conditions, all of which may be optimized for effective cooling.

Figure 6:
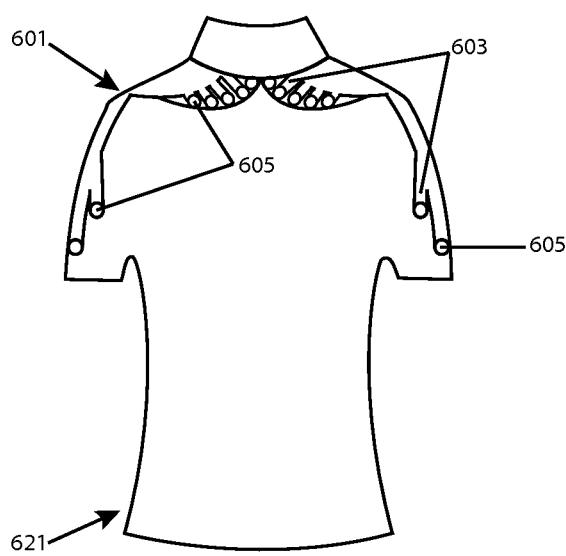
FIG. 6 is a rear view of another garment previously pictured—this time, the short-sleeved garment previously pictured in FIG. 2.

As with FIG. 5, FIG. 6 provides a rear view of a garment previously pictured—this time, the short-sleeved garment previously pictured in FIG. 2. Thus, as with FIG. 2, FIG. 6 illustrates a garment including a variable coolant deployment matrix 601 within a short-sleeved athletic garment 621 for a trained female athlete user. Also as with FIG. 5, the distribution of variably-opening and or coolant-releasing, -channeling or passing conduits, such as the examples shown as 603, and ports, examples of which are shown as 605, from the rear view, exhibit an exemplary optimized distribution throughout the garment, but now for the rear of the garment and user's body, as well as other factors discussed previously. A large distribution of those conduits and ports again are included to provide cooling fluid to the upper back region. However, slight optimizing adjustments are reflected, for such factors affecting optimized distribution that were discussed previously, and elsewhere in this application. For example, even more supply of coolant may be released in the upper back region, because the ports and conduits supplying cooling to the user's forearms stop short of the cuff of the short sleeves—similarly to FIG. 2, depicting the front of the garment—and coverage of some cooling optimized areas of the garment and the user's body is preferably supplied from a different source.

Figure 7:
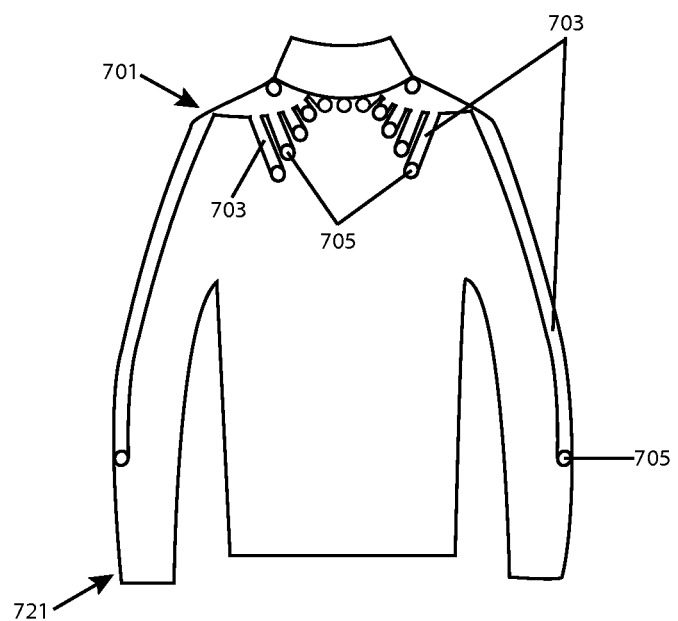
FIG. 7 is a rear view of another garment previously pictured, for male users—this time, the long-sleeved garment previously pictured in FIG. 3.
Figure 8:
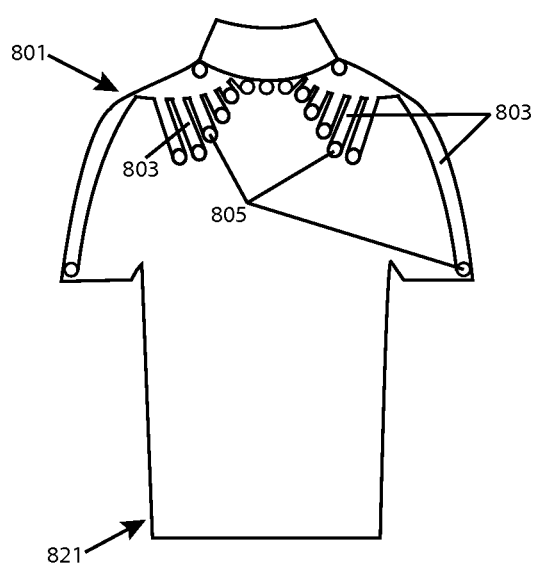
FIG. 8 is a rear view of another garment previously pictured, for male users—this time, the short-sleeved garment previously pictured in FIG. 4.

FIGS. 7 and 8 depict rear views of the same long- and short-sleeved garments with coolant matrices depicted previously from a front view in FIGS. 3 and 4, respectively. Again, those garments and matrices are optimized for trained male athletes, as discussed above, providing optimal, timely coverage of coolant fluid to effective areas of the user's body. Similarly to the rear aspects of the garments for female athletes discussed above, the distribution provides a great deal of coverage of the user's upper back. In addition, the distribution of the matrix covers a wider range of the user's back, and emphasizes the scapula, but provides less coverage of the user's forearm, reflecting data indicating that such a distribution is more optimal for trained male athlete users.

Although FIGS. 1-8, above, have dealt with trained athlete users only, and upper-body cooling garments and matrices, it should be understood that aspects of the present invention apply to a wide variety of possible human and non-human users, and to a wide variety of different garments, including, but not limited to, pants, shorts, skirts, jackets, athletic footwear, wristbands, swimwear, undergarments and headwear. For example, if the cooling garment is shorts or a skirt, a distribution of cooling conduits and ports should provide timely coolant coverage to user's thighs, if the user is athletically trained, to a higher degree than the user's rear legs and shins. This is based on data for both sexes indicating that trained individuals benefit from evaporative cooling in those regions. In addition, where sensitive areas, or other areas that may suffer adverse effects from the ports and/or conduits, such ports and conduits should be omitted in areas leading to coverage of those sensitive regions (for example, gravitationally above a user's eyes, in the instance of a headband or hat as a matrix-associated garment). Also, where the fluid may compromise athletic performance, for example, by reducing grip, a an offsetting (e.g., grip-enhancing) agent or other formulation component may be added, or the coolant may be omitted in regions leading to coverage of the user's palms, or other cutaneous gripping regions or other adversely affected regons—by the matrix, garment, system (which may include a control system) and/or user. If a user is not undergoing physical exertion, but, instead, is in a resting or other state, the matrix and garment and coolant deployment techniques may also, variably selectably by design, a system and/or user, differ from the optimizations set forth above. For example, while laying in a supine position, the cooling techniques may first emphasize caudal, then, to a later and/or lesser degree, rostral coolant fluid deployment, based on data indicating that that pattern may be more optimal under those conditions.

Figure 9:
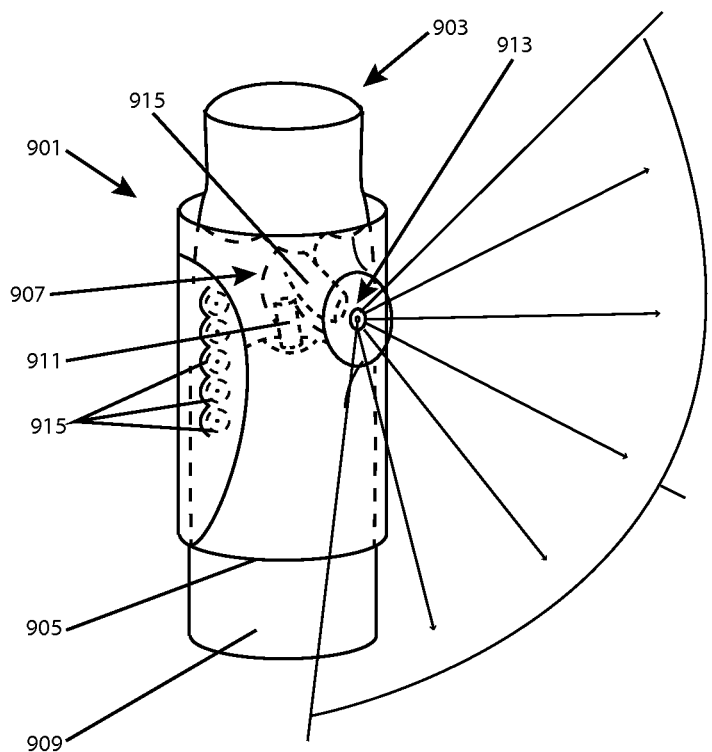
FIG. 9 is a perspective view of an exemplary coolant fluid container and deployment device.

FIG. 9 is a perspective view of an exemplary coolant fluid container and deployment device 901. A rounded pushbutton 903 is accessible to a human user and actuable by downward pressure (for example, digital pressure). Ideally, a user would use his or her thumb to depress pushbutton 903, while gripping the generally cylindrical housing 905 of the device 901 with his or her fingers of the same hand. In so actuating the device with pushbutton 903, a release mechanism or pump 907 causes coolant fluid to be released from an exchangeable coolant fluid reservoir 909. Preferably, reservoir 909 is pressurized with a propellant, and is releasable from the reservoir by sideward and/or downward pressure on a valve stem 911. In this way, downward or sideward pressure against the stem 911 from mechanism or pump 907 (driven by connected pushbutton 903) leads to the release of coolant through and out of a diffusing spray nozzle 913. The user may direct the flow of such coolant fluid, in a sprayed and/or aerosolized stream, at regions that he or she desires to cool or create a cooling sensation, for example, while exercising.

The release mechanism or pump 907 is preferably of a new type that increases flow with greater pressure by the user against pushbutton 903, but that also widens the directional range of the spray with that same greater pressure, and vice versa in both respects for lightened pushbutton pressure. For example, as pictured in FIG. 9, a bent but otherwise roughly cylindrical, or other curved piece 915, may be driven both downward and against stem 911 when pushbutton 903 is depressed by a user. Thus, greater pushbutton pressure leads to greater sideward and downward pressure against the stem, driving more coolant out of vessel 909. At the same time, however, the end of the roughly cylindrical piece 915 is driven closer to the exit port of nozzle 913, leading it to increase its sideways dispersion of emitted coolant fluid.

Figure 9A:
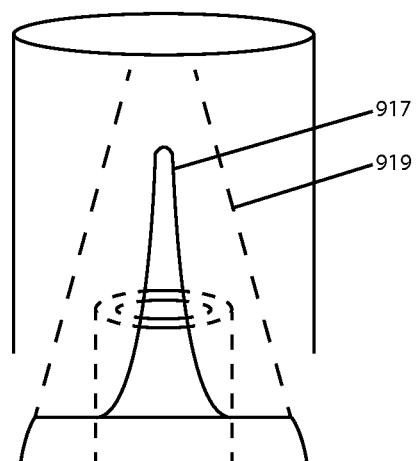
FIG. 9a is a partial perspective view of an alternative embodiment of a fluid container and deployment device sub-structure for releasing pressurized coolant fluid—namely, a descending notch attachment to a coolant release pushbutton.

As an alternative mechanism, which is also illustrative, not exhaustive, of aspects of the present invention, FIG. 9a is a partial perspective drawing of a descending notch attachment to a coolant release pushbutton. A notch 917 that narrows upwardly along its vertical length may be depressed downward, along with an angle-walled pocket 919 with a fluid escape toward the notch 917, in communication with the notch 917. Greater downward pressure will lead to greater pressure and amount of fluid release, but also diminishing width of the used notch, leading to greater diffusion of coolant fluid.

Although not preferred in all embodiments, the housing 905 may contain partially-inward facing (dousing the housing and user's hands holding the housing) nozzle(s) 915. Thus, the release mechanism or pump 907, including it's coolant-guiding surfaces, may partly divert released spray from stem 911 onto the handle/housing 905 and the user's hands, to aid in cooling them. In some embodiments, for example, with coolant including antimicrobial or soap agents, this aspect may also assist in cleaning the housing 905 during and after use. For example, a more delayed route for coolant ejected from nozzles 915 may lead the housing to be cleaned after use, rather than just during use.

Figure 10:
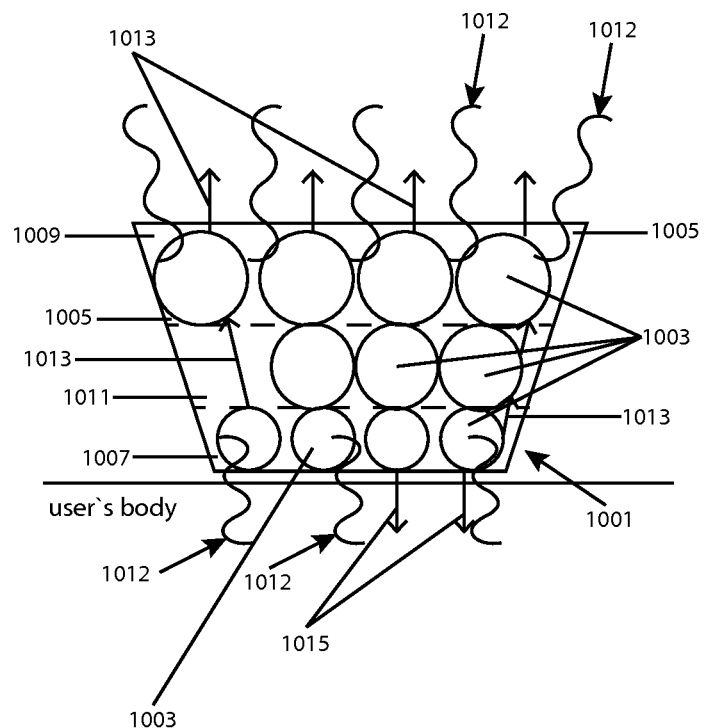
FIG. 10 is a side view of a garment sub-structure with advanced thermal conductive and transpiration properties, for use with cooling fluids, systems and other cooling techniques.

FIG. 10 depicts a new form of garment sub-structure with advanced thermal conductive and transpiration properties, for use with the cooling fluids, systems and other techniques set forth above. A thermal conduction cell 1001 includes a plurality of thermally-conductive sub-structures, such as those examples shown as 1003, immersed in a thermally-conductive gel, liquid or other matrix 1005. In some embodiments, the matrix 1005 is composed of three layers of gel, liquid or other matrix components, one of which (pictured as 1007) is locally thermally conductive and drawn toward the proximal (closest to the user's body) side of cell 1001, another of which (pictured as 1009) is thermally conductive and drawn toward the distal side of cell 1001, and a third (pictured as 1011) that is thermally insulating and generally divides the other two layers. The mechanism for drawing these layers to their respective locations may be magnetism or the polarity of the matrix compositions, and/or the colligative or other bonding properties of those compositions as they may interact with the walls of the cell 1001. As a user of the garment generates heat from his or her body, that heat will be transferred to and absorbed by the substructures 1003 that are closest to the proximal side of cell 1001. To aid in this energy transfer, thermally conductive flexible filaments or other members (examples of which are pictured as 1012) embedded in the proximal and distal walls of cell 1001 may conform to the surface of the user's body and the substructures 1003, and create a large thermally interactive surface area in both respects. As substructures 1003 absorb body heat from the user, they may increase in size and, in so doing, begin to exceed the width of at least two sloped walls of cell 1001 which face one another, at the proximal points closer to the user. As this occurs, each such substructure 1003 is forced upward, as demonstrated by force arrows, examples of which are shown as 1013, and toward the distal side of cell 1001, preferably with the aid of a lubricant within the cell matrix 1005, and interacts with thermally conductive structures on that distal side of the cell 1001, transferring heat into the atmosphere surrounding the user and garment. To aid in this process, a cooling gel, that may operate by transpiration, may be applied to that distal side of the cell, for example, by the techniques for distributing cooling gels and formulations of cooling gels discussed elsewhere in this application. As the substructures 1003 cool down, they become smaller and, as such, are able once again to pass back to the proximal side of cell 1001, as shown by force/motion arrows 1015, and are forced to do so by displacement by other substructures that are subsequently heated and driven distally outward, colliding with them. In this way, the thermally-conductive substructures rapidly draw heat away from the user's skin, and replacing themselves with cooler units proximal to the user's skin, and maintain a high thermal differential for increased cooling. Although the sloped walls facing one another that lead to heated substructures 1003 moving distally do not permit the substructures to pass back in the proximal direction until cooled down, other walls of cell 1001 are preferably wide enough apart to permit substructures 1003 to exchange places, and move past one another within the cell 1001.

Figure 11:
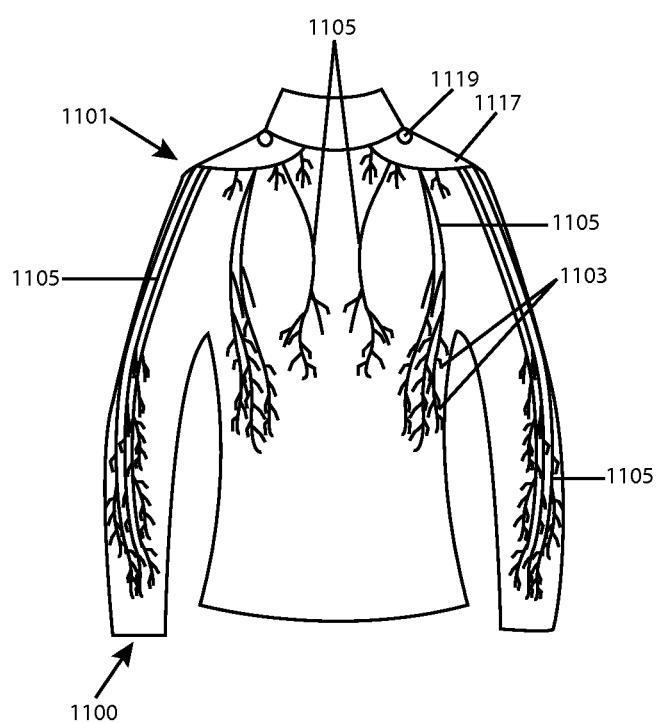
FIG. 11 is a front view of a long-sleeved garment for a female athlete, including a more diffuse, and preferred, variable coolant deployment matrix, in accordance with aspects of the present invention.

FIG. 11 is a front view of a long-sleeved garment 1100 for a female athlete, including a more diffuse, and preferred, variable coolant deployment matrix 1101, in accordance with aspects of the present invention. The regions receiving a heavier deployment at terminal ends of channels, 1103, than other regions bear a resemblance to analogous counterpart channels in FIG. 1. However, the channels themselves are smaller, greater in number and more diffuse, with a greater number of potentially variable openings at a wider array of points along the lengths of the channels. As a result, the channels, such as those examples provided as 1105, may become more integral, flexible, stretchable, and conformable to the characteristics of the athletic garment, and individual needs of the athlete wearing the garment and/or matrix. Also because they are smaller and more diffuse, the channels and terminal ports may become less noticeable and nettlesome to a user, and may more easily integrate with the fabric of garment. In addition, a far wider surface area for diffusion of coolant fluid is achieved, with much greater cooling efficiency. In some embodiments, the matrix may be woven into the fabric of the garment itself, and customizable to the extent that the garment itself is. Thus, whereas previous figures illustrated simplified exemplary matrices and/or garments for ease of discussion, FIG. 11 demonstrates a coolant fluid diffusion network closer to a preferred embodiment. An even more preferred embodiment, with a greater number of even smaller channels might be imperceptible to the user, except for the cooling effect, because the channels are small enough to be invisible to the naked eye, or even disappear into the weave of the garment. The reservoirs, such as the example pictured as 1117, may also be more diffuse, or omitted in favor of local storage within channels 1105 only, although a central resealable refilling port, such as that pictures as 1119, is still preferred.

It is within the scope of this invention that a similar distribution matrix may be used in conjunction with agents for purposes other than cooling, some of which agents and purposes are discussed above. To the extent that the emphasis for these other objectives differ, the optimal distribution patter of the matrix may also varry to access those regions of a user's body that most benefit from the agent(s) in use in the medium distributed via the matrix. For example, a heating fluid, releasing chemically-released heat through such a matrix, may target those regions demonstrated to benefit from rehabilitative heat sources, in a particular matrix. Similarly, a gripping agent fluid (as discussed above) may target regions in need of greater cutaneous grip (e.g., the palms of the hands, or bottom surface of athletic shoes). Although this application has stressed flexible tubing and channels with releasing ports or spray nozzles for releasing fluid, any method of application or distribution of fluid (either directly, or through other intermediate media or devices) may be used.

I claim:

1. A network or matrix of coolant fluid transporting conduits mounted in, on or about a garment, comprising at least one coolant fluid containing conduit and at least one openable port(s), placed at a location(s) such that, when coolant fluid is released from said port(s), it will be guided more predominantly onto at least one first region of a human or other animal's body which at least one first region is a more effective medium for transpiration cooling of said body than at least one second region of said body, wherein triggering to release coolant fluid from the openable port(s) is by thermodynamic expansion of a ring or other shaped structure within the openable port(s), wherein the ring or the other shaped structure comprises a thermally expanding material.

2. The network or matrix of coolant fluid-transporting conduits mounted in, on or about a garment of claim 1, in which the matrix further comprises at least one storage vessel for said coolant fluid that may be loaded with coolant fluid by a user, prior to distribution of the coolant fluid at least partially by said matrix.

3. The network or matrix of coolant fluid-transporting conduits mounted in, on or about a garment of claim 1, wherein the ring or the other shaped structure is connected to another ring that is elastomeric and which said another ring comprises a hole that opens with said thermodynamic expansion of the ring or the other shaped structure.

4. The network or matrix of coolant fluid transporting conduits mounted in, on or about a garment of claim 1, wherein said at least one openable port(s) is also configured to be triggered to release coolant fluid by user actuation.

5. The network or matrix of coolant fluid transporting conduits mounted in, on or about a garment of claim 1, wherein said thermally expanding material is from the group consisting of light metals, alloys of light metals and elastomeric materials.

6. The network or matrix of coolant fluid transporting conduits mounted in, on or about a garment of claim 1, wherein said thermodynamic expansion is caused at least in part by a user's body.

7. The network or matrix of coolant fluid transporting conduits mounted in, on or about a garment of claim 1, wherein said thermodynamic expansion is caused at least in part by a user's body and said triggering to release coolant fluid by said thermodynamic expansion is by a structure comprised in said ring or other shaped structure that may define or open and/or an opening.

8. The network or matrix of coolant fluid-transporting conduits mounted in, on or about a garment of claim 1, further comprising serial addition of the expansion of individual expanding sub-members comprised in said ring or said other shaped structure.

9. The network or matrix of coolant fluid-transporting conduits mounted in, on or about a garment of claim 1, wherein said at least one first region comprises the forearms and/or upper back of a user of said network or matrix.

10. The network or matrix of coolant fluid-transporting conduits mounted in, on or about a garment of claim 2, wherein said at least one first region comprises the forearms and/or upper back of a user of said network or matrix, and said forearms and/or upper back receive a greater amount of coolant fluid per unit of surface area than at least one other region.

11. A method for storing and distributing a coolant fluid, comprising the following steps:
(1) creating or acquiring a garment comprising a network of conduits mounted in, on or about said garment, which network of conduits further comprises at least one coolant fluid containing conduit and at least one openable port(s) at a location(s) such that, when coolant fluid is released from said port(s), it will be guided more predominantly onto at least one first region of a human or other animal's body which at least one first region is a more effective medium for transpiration cooling of said body than at least one second region of said body, wherein triggering to release coolant fluid from the openable port(s) is by thermodynamic expansion of a ring or other shaped structure within the openable port(s), wherein the ring or the other shaped structure comprises a thermally expanding material;
(2) introducing a coolant fluid into said network of conduits;
(3) releasing some of said coolant fluid introduced into said network of conduits, onto a human or other animal body, targeting said at least one first region.

12. The method for storing and distributing coolant fluid of claim 11, comprising the following additional step:
creating or acquiring an additional storage vessel for coolant fluid, which vessel is loaded or loadable with coolant fluid by a user.

13. The method for storing and distributing a coolant fluid of claim 11, comprising the following additional step:
at least one of said openable port(s) is triggered to release coolant fluid by a change in temperature due to a local or other environmental cause of that change in temperature.

14. The method for storing and distributing a coolant fluid of claim 11, comprising the following additional step:
at least one of said openable port(s) is also configured to be triggered to release coolant fluid by-user actuaction.

15. The method for storing and distributing a coolant fluid of claim 13, comprising the following additional step:
said change in temperature is induced at least in part by a user's body.

16. The method for storing and distributing a coolant fluid of claim 15, wherein the at least one conduit further comprises a closing device of said openable port(s) that has a volume that is thermodynamically altered, and said closing device comprises an expandable piece defining an opening.

17. The method for storing and distributing a coolant fluid of claim 13, comprising the following additional step:
a coolant fluid with a volatility greater than that of water is introduced into said network of conduits or onto the surface of a human body.

18. The method for storing and distributing a coolant fluid of claim 16, comprising the following additional step:
a plurality of individual expanding sub-members are comprised in said expandable piece.

19. The method for storing and distributing a coolant fluid of claim 11, wherein the targeting comprises targeting the cooling fluid from the network of conduits to said at least one first region comprising forearms and/or upper back of a user; and regions not comprising the forearms and/or upper back of a user of said network or matrix are avoided or untargeted in said targeting.

20. The method for storing and distributing a coolant fluid of claim 11, wherein the ring or the other shaped structure is connected to another ring that is elastomeric and which said another ring comprises a hole that opens with said expansion of the ring or the other shaped structure.

21. The method for storing and distributing a coolant fluid of claim 11, wherein said thermally expanding material is from the group consisting of light metals, alloys of light metals and elastomeric materials.

* * * * *